(12) United States Patent
Klemm (10) Patent No.: US 11,744,488 B2
(45) Date of Patent: Sep. 5, 2023

(54) NFC GLUCOMETER CONTAINING RECHARGEABLE BATTERY

(71) Applicant: SANOFI, Paris (FR)

(72) Inventor: Thomas Klemm, Frankfurt am Main (DE)

(73) Assignee: Sanofi, Paris (FR)

( * ) Notice: Subject to any disclaimer, the term of this patent is extended or adjusted under 35 U.S.C. 154(b) by 296 days.

(21) Appl. No.: 16/954,378

(22) PCT Filed: Dec. 17, 2018

(86) PCT No.: PCT/EP2018/085114
§ 371 (c)(1),
(2) Date: Jun. 16, 2020

(87) PCT Pub. No.: WO2019/121450
PCT Pub. Date: Jun. 27, 2019

(65) Prior Publication Data
US 2021/0080451 A1    Mar. 18, 2021

(30) Foreign Application Priority Data
Dec. 18, 2017    (EP) .................................... 17306807

(51) Int. Cl.
*H02J 50/10* (2016.01)
*A61B 5/145* (2006.01)
(Continued)

(52) U.S. Cl.
CPC ... *A61B 5/14532* (2013.01); *G01N 33/48785* (2013.01); *G01N 33/66* (2013.01);
(Continued)

(58) Field of Classification Search
CPC .................................................... H02J 50/20
(Continued)

(56) References Cited

U.S. PATENT DOCUMENTS

| 7,965,180 B2 | 6/2011 | Koyama |
| 9,197,082 B1 | 11/2015 | Zhang |
| (Continued) | | |

FOREIGN PATENT DOCUMENTS

| CN | 2728513 | 9/2005 |
| CN | 104066467 | 9/2014 |
| (Continued) | | |

OTHER PUBLICATIONS

Freudenthal et al., "Suitability of NFC for Medical Device Communication and Power Delivery," IEEE Dallas Engineering in Medicine and Biology Workshop, Nov. 11, 2007, pp. 51-54.
(Continued)

*Primary Examiner* — Yalkew Fantu
(74) *Attorney, Agent, or Firm* — Fish & Richardson P.C.

(57) ABSTRACT

The disclosure refers to a medical device comprising a measurement unit adapted to measure a value of a physiological parameter, for example a blood glucose level, an energy storage unit providing energy supply for the measurement unit, an NFC antenna, an energy supply unit that controls the NFC antenna such that in the presence of an electromagnetic field of a pre-defined frequency range energy is withdrawn from the electromagnetic field surrounding the NFC antenna and stored in the energy storage unit, a charge control unit adapted to determine the electric charge contained in the energy storage unit, and a communication unit adapted to output a pre-defined visible, audible and/or tactile signal if the electric charge contained in the energy storage unit determined by the charge control unit is equal to or below a pre-defined minimum charge value.

20 Claims, 4 Drawing Sheets

(51) Int. Cl.
*H02J 50/20* (2016.01)
*H02J 7/00* (2006.01)
*G01N 33/487* (2006.01)
*G01N 33/66* (2006.01)
*H01M 10/44* (2006.01)
*H02J 7/34* (2006.01)

(52) U.S. Cl.
CPC ......... *H01M 10/44* (2013.01); *H02J 7/00032* (2020.01); *H02J 7/0048* (2020.01); *H02J 50/10* (2016.02); *H02J 50/20* (2016.02); *H01M 2220/30* (2013.01); *H02J 7/345* (2013.01)

(58) Field of Classification Search
USPC ......................................................... 424/450
See application file for complete search history.

(56) References Cited

U.S. PATENT DOCUMENTS

| | | | |
|---|---|---|---|
| 11,524,122 | B2 | 12/2022 | Hammen et al. |
| 2005/0038332 | A1 | 2/2005 | Saidara et al. |
| 2011/0313395 | A1 | 12/2011 | Krulevitch et al. |
| 2012/0268741 | A1 | 10/2012 | Pommereau et al. |
| 2013/0161985 | A1* | 6/2013 | Fukawatase ............. B60N 2/42 280/730.2 |
| 2013/0324920 | A1 | 12/2013 | Kohli et al. |
| 2015/0048836 | A1* | 2/2015 | Guthrie ............... H01M 6/5083 324/427 |
| 2016/0008541 | A1 | 1/2016 | Hirschel et al. |
| 2016/0161985 | A1* | 6/2016 | Zhang .................. G16H 20/17 600/595 |
| 2017/0055890 | A1* | 3/2017 | Kube ..................... H02J 50/05 |
| 2017/0331309 | A1 | 11/2017 | Gofman et al. |
| 2017/0347927 | A1* | 12/2017 | He ..................... A61B 5/14503 |
| 2019/0388619 | A1 | 12/2019 | Hammen et al. |
| 2020/0275867 | A1* | 9/2020 | Klemm ................. A61B 5/076 |
| 2023/0011040 | A1 | 1/2023 | Hammen et al. |

FOREIGN PATENT DOCUMENTS

| | | |
|---|---|---|
| CN | 105209091 | 12/2015 |
| EP | 2190504 | 1/2014 |
| JP | 2013-135557 | 7/2013 |
| JP | 2015-518747 | 7/2015 |
| JP | 2017-505648 | 2/2017 |
| JP | 2017-196423 | 11/2017 |
| WO | WO 2009/032402 | 3/2009 |
| WO | WO 2013/063634 | 5/2013 |
| WO | WO 2013/085453 | 6/2013 |
| WO | WO 2013/177135 | 11/2013 |
| WO | WO 2014/184080 | 11/2014 |
| WO | WO 2015/102740 | 7/2015 |
| WO | WO 2015/136564 | 9/2015 |
| WO | WO 2016/019375 | 2/2016 |
| WO | WO 2016/055400 | 4/2016 |
| WO | WO 2016/110592 | 7/2016 |
| WO | WO 2016/142216 | 9/2016 |
| WO | WO 2016/166338 | 10/2016 |

OTHER PUBLICATIONS

PCT International Preliminary Report on Patentability in International Appln. No. PCT/EP2018/085114, dated Jun. 23, 2020, 12 pages.

PCT International Search Report and Written Opinion in International Appln. No. PCT/EP2018/085114, dated Feb. 19, 2019, 18 pages.

* cited by examiner

NFC GLUCOMETER CONTAINING RECHARGEABLE BATTERY

CROSS REFERENCE TO RELATED APPLICATIONS

The present application is the national stage entry of International Patent Application No. PCT/EP2018/085114, filed on Dec. 17, 2018, and claims priority to Application No. EP 17306807.3, filed on Dec. 18, 2017, the disclosures of which are incorporated herein by reference.

TECHNICAL FIELD

The present disclosure relates to a medical device for supporting health control and an operation method for such medical device.

BACKGROUND

The following description of the present disclosure mainly refers to diabetes as a health problem and the blood glucose level as the physiological parameter to be controlled in order to assess the effectiveness of the prescribed treatment. However, the present disclosure may also be used with regard to other health problems and for management of other physiological parameter data like (a) blood pressure in hypertensive heart disease, (b) cholesterol or lipoprotein profile in patients with risk factors for heart disease and stroke, (c) peak flow in asthmatic patients, or (d) coagulation in patients treated for hemophilia.

Diabetes mellitus is a group of metabolic diseases in which a person has high blood sugar, either because the pancreas does not produce enough insulin, or because cells do not respond to the insulin that is produced. The treatment of diabetes concentrates on keeping blood sugar levels as close to normal ("euglycemia") as possible, without causing hypoglycemia. This can usually be accomplished with diet, exercise, and use of appropriate medications (insulin in the case of type 1 diabetes; oral medications, as well as possibly insulin, in type 2 diabetes).

Essential elements of the management of diabetes with insulin are periodic checks of the glucose concentration in the blood performed by the patients themselves, in order to obtain regular information on the progress and success of the prescribed treatment. This understanding, and patient participation is vital, since the complications of diabetes are far less common and less severe in patients who have well-managed blood sugar levels. With regard to this it has to be considered that the blood glucose level fluctuates throughout the day and is directly influenced by the amount of insulin administered, as well as lifestyle factors such as the amount and kind of food that is consumed, the exercise level and stress.

Therefore, the monitoring of the sugar level in the blood serves a dual purpose: on the one hand it provides the patient with information about the current status of glycemic control. On the other hand can the measured values serve as information for the patient or a healthcare professional (HCP) to determine whether an adjustment in the medication, for example the amount of insulin to be taken, is indicated.

In order to achieve these goals or to get as close as possible to the desired glycemic control, it is common practice that blood glucose measurement values are monitored once or several times during the day using a blood glucose meter (BGM), following a testing regime normally prescribed by an HCP. A BGM usually comprises an energy storage unit which provides supply voltage to a display and/or another communication unit, a memory and a measurement unit and/or other elements of the BGM. The energy storage unit may be charged using NFC (near field control). NFC is rooted in radio-frequency identification technology (known as RFID) which allows compatible hardware to both supply power to and communicate with an otherwise unpowered and passive electronic tag using radio waves. This is used for energy supply, identification, authentication and tracking.

The document WO 2013/063634 A1 relates to a measurement device for measuring glucose, comprising: a glucose sensor for determining the glucose content in a solution or fluid, in particular in blood, and for reproducing the measured glucose content in the form of an electrical signal with measurement data presented in encoded form; an NFC antenna; an energy withdrawal unit downstream of the NFC antenna, which controls the NFC antenna in such a way that the NFC antenna withdraws energy from the field surrounding the NFC antenna if electromagnetic waves in a predetermined frequency range are present, and wherein the NFC antenna is upstream of the glucose sensor and supplies it with electrical energy.

In order to realize sufficient health control such BGM needs to be ready for operation at the time the measurements of the physiological parameter are needed or scheduled. For adequate measurement using BGM by NFC a sufficient amount of energy in the form of voltage and/or charge to power is required during the measurement, for example a charge of 30 mAs for one glucose measurement. If the current measurement is influenced by too little charge and/or voltage an NFC demolition is to be expected which may potentially cause false blood glucose measurement values.

SUMMARY

In certain aspects, a medical device in which the blood glucose measurement or the measurement of other physiological parameter is not influenced by low voltage and/or charge is provided.

In particular, according to the present disclosure the medical device may comprise
- measurement unit adapted to measure a value of a physiological parameter, for example a blood glucose level,
- an energy storage unit connected with the measurement unit providing energy supply for the measurement unit,
- an internal NFC antenna,
- an energy supply unit connected with the NFC antenna and with the energy storage unit, wherein the energy supply unit controls the NFC antenna such that in the presence of an electromagnetic field of a pre-defined frequency range energy is withdrawn from the electromagnetic field surrounding the NFC antenna and stored in the energy storage unit,
- a charge control unit, connected to the energy storage unit and adapted to determine the electric charge contained in the energy storage unit, and
- a communication unit connected with the charge control unit, wherein the communication unit is adapted to output a pre-defined visible, audible and/or tactile signal if the electric charge contained in the energy storage unit determined by the charge control unit is equal or below a pre-defined minimum charge value.

Using the above medical device comprising the NFC antenna, the energy supply unit and the charge control unit it can be avoided to conduct a measurement of a physiological parameter (e.g. a blood glucose measurement) in case too little voltage and/or charge is contained in the energy storage unit as the communication unit communicates that the device is not operational. Determination of false measurement values is thereby avoided. The measurement unit may be adapted such that a determination of a value of the physiological parameter by the measurement unit may be blocked if the if the electric charge contained in the energy storage unit determined by the charge control unit is equal to or below the pre-defined minimum charge value.

According to one embodiment the energy storage unit may be a rechargeable battery or a capacitor with a very large capacity (X5R or Super-Cap).

In one embodiment the NFC antenna (also referred to as internal antenna) may have a dimension of 3×3×0.5 cm, and may provide a maximum of 3 mA at 3 V.

For energy supply an external NFC antenna of a mobile phone or smart phone or another charging device may be used.

According to the present disclosure NFC is a set of short-range wireless technologies, typically requiring a separation of 10 cm or less. NFC operates at 13.56 MHz on ISO/IEC 18000-3 air interface and at rates ranging from 106 kbit/s to 424 kbit/s. NFC always involves an initiator and a target; the initiator actively generates an RF field that can power a passive target. This enables NFC targets to take very simple form factors such as unpowered tags, stickers, key fobs, or cards. NFC peer-to-peer communication is possible, provided both devices are powered. NFC standards are based on existing RFID standards including ISO/IEC 14443, 18092 and those defined by the NFC Forum. NFC is standardized for example in ECMA-340 and ISO/IEC 18092.

In an embodiment the charge control unit comprises a gas gauge. The gas gauge (also referred to as fuel gauge or Coulomb counter) may be used in the electronic field for the load count in an energy supply unit such as a rechargeable battery, similar to the tank meter in the car. It comprises a resistor having very low resistance and determines the integral over the electric current flowing through the resistor (or voltage drop over the resistor as equivalent) in order to determine the electric charge contained in the energy supply unit. The gas gauge further may comprise an A/D converter, a counter and may be connected to a clock unit. The A/D converter converts the measured voltage drop over the resistor into an A/D converter count which reflects the level of current and its direction within a pre-defined time period provided by the clock unit. High current causes an accelerated increase of the counter value and indicates a high electric charge and low current a low increase indicating a low electric charge contained in the energy supply unit. Negative current causes a decrease in the counter value and indicates the discharge mode of the energy supply unit.

In another embodiment the charge control unit continuously observes time-dependent change in the voltage drop over the energy supply unit, which is, for example, a capacitor. In this case each charging and decharging step causes a change in the voltage drop over the capacitor. The charge control unit observes the development of the voltage drop over time thereby determining the amount of charge flowing to or from the capacitor based on the continuous observation of the voltage drop and the well-known relation $Q=C\times U$, wherein U is the voltage, C is the capacity of the capacitor and Q is the charge.

In another embodiment the NFC antenna comprises a ferrit core or disc in order provide a more efficient charging. Ferrites are electrically bad or non-conductive ferromagnetic ceramic materials from the iron oxide hematite ($Fe_2O_3$), rarely of magnetite ($Fe_3O_4$) and other metal oxides. Depending on the composition ferrites are magnetically hard or magnetically soft.

In an embodiment the NFC antenna and/or the ferrit core or disc is formed by a structure printed on a PCB (Printed circuit board).

In further embodiments at least one of the following features may be included:
  a solar cell connected with the energy storage unit for an additional energy supply, the solar cell may be integrated in the PCB,
  the measurement unit may provide an integrated A1c estimation algorithm,
  the device may be sealed such that it can be cleaned with a detergent capable MRSA,
  the device may comprise an integrated temperature tracker which checks the temperature continuously, wherein a temperature below and equal to a minimum temperature value or a temperature above and equal to a maximum temperature value (the maximum temperature value is greater than the minimum temperature value) prevents the user to conduct a measurement of the physiological parameter in order to avoid false measurement values,
  the device may comprise an interface to an NFC insulin managing device in order to act independently from a mobile device,
  the device may provide a management of BGM data,
  the device may display measured or stored BGM data as well as BGM target data,
  the interface of the device may provide a connection to an app, cloud, HCP data base as well as access to this data base.

The device may be further adapted to administrate a medicament (i.e. additionally works as a drug delivery device) based on the measured value or values of the physiological parameter, e.g. the measured blood glucose values, for example the recently measured value or the values measured over a pre-defined time period.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(w-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten. An examples of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The disclosure further refers to a method for operation a medical device according to the above explained embodiments, which comprises the following steps:

determining the electric charge contained in the energy storage unit before one measurement of the physiological parameter is conducted by the measurement unit, measuring the physiological parameter using the measurement unit if the electric charge contained in the energy storage unit determined by the charge control unit greater than a pre-defined minimum charge value, or output a pre-defined visible, audible and/or tactile signal by the communication unit if the electric charge contained in the energy storage unit determined by the charge control unit is equal to or below the pre-defined minimum charge value.

In one embodiment the method further comprises the step of activating the energy supply unit for energy withdrawal using the NFC antenna if the electric charge contained in the energy storage unit determined by the charge control unit is equal to or below the pre-defined minimum charge value.

The above method reduces the risk of determination of false measurement values as well.

BRIEF DESCRIPTION OF THE FIGURES

Exemplary embodiments of the present disclosure are described herein with reference to schematic drawings, in which.

DETAILED DESCRIPTION

The following paragraphs will describe various embodiments of the present disclosure. For exemplary purpose only, the embodiments are outlined in relation to a medical device supporting health control measuring a blood glucose value and its operation method. However, the used terminology and the description of the embodiments with respect to the medical device or health indicating method are not intended to limit the principles and ideas of the present disclosure to such a single device or method and may be adapted to other physiological values accordingly.

Figure 1:
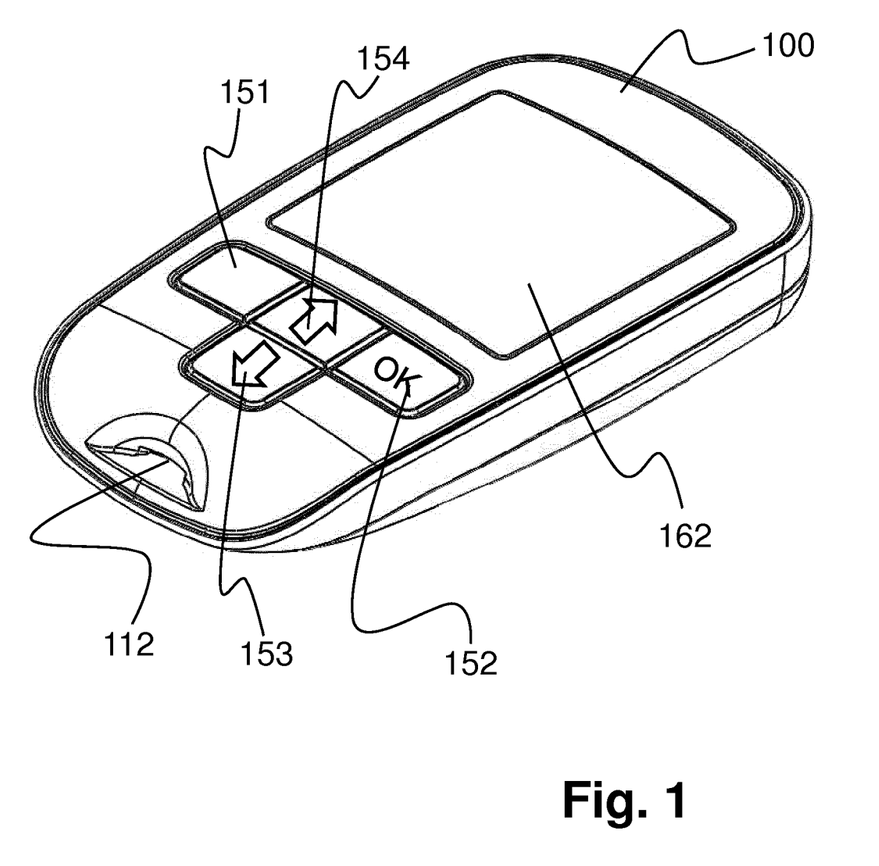
FIG. 1 shows the medical device according to an embodiment of the present disclosure in a perspective view.
Figure 2:
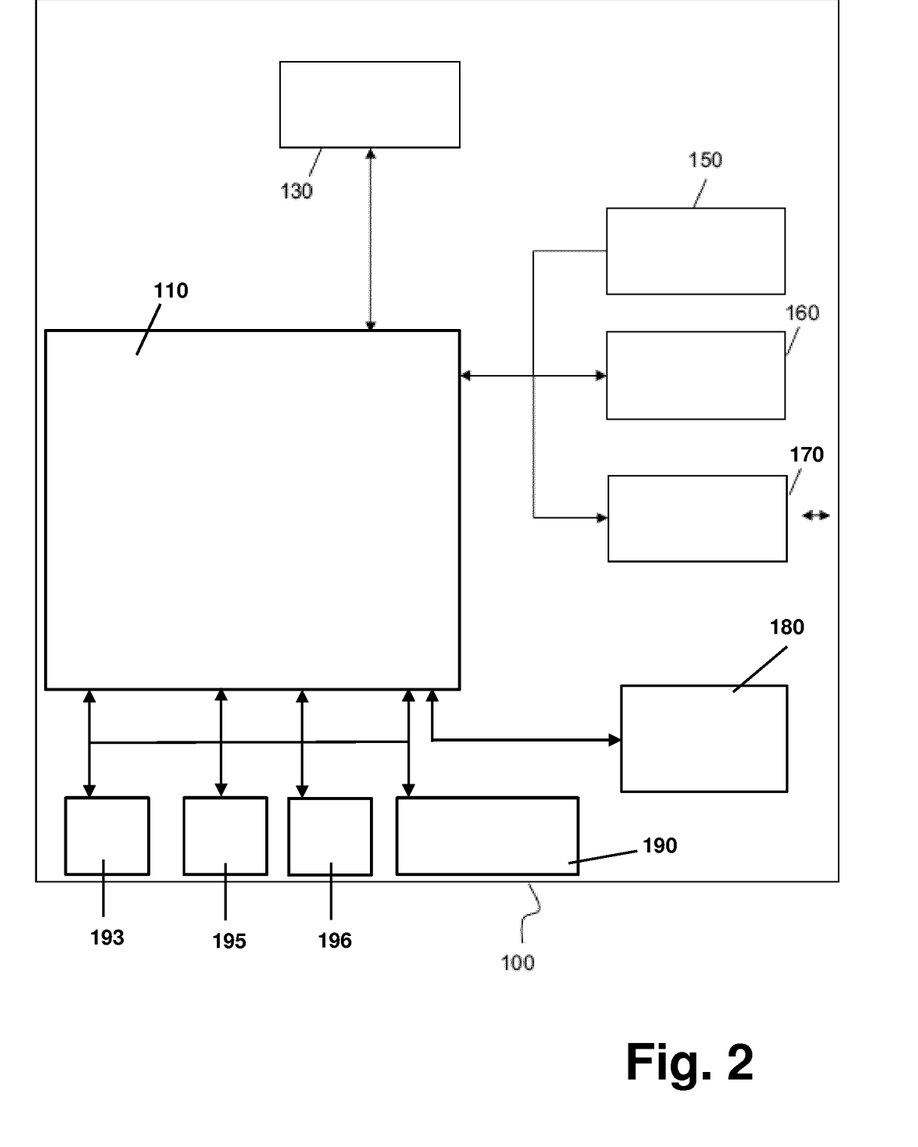
FIG. 2 shows a diagram of the medical device as shown in FIG. 1.

FIG. 1 is a schematic drawing and FIG. 2 is a schematic diagram of the medical device 100 according to an embodiment of the present disclosure. The medical device 100 comprises a blood glucose measurement unit 110, which is arranged to measure the blood glucose level and data processing. Further, the measurement unit 110 comprises an interface and a slot 112 for inserting a test strip.

The blood glucose measurement unit 110 may forward e.g. blood glucose measurement data to a data storage 130 (storage unit or means) or memory, such as a Flash memory. Alternatively, the blood glucose measurement unit 110 may retrieve stored data such as e.g. blood glucose value data from the data storage 130. The blood glucose measurement unit further comprises a processor (processing unit or means), such as a microcontroller or microprocessor, a digital signal processor, and/or the like for data processing.

The blood glucose measurement unit 110 is further connected to a user input unit 150 of a user interface. The user input unit 150 is arranged to receive input from the user of the medical device 100 for example by key 151, confirmation key (OK button) 152, key 153 for scrolling down (downward button) and key 154 for scrolling up (upward button). The user input data are forwarded from the user input unit 150 to the blood glucose measurement unit 110, which may forward it to the processor and/or to the data storage 130.

Furthermore, the user interface of medical device 100 comprises a display unit 160 with a display 162, which is connected to the blood glucose measurement unit 110 as well. The display unit 160 may receive data to be displayed by the display 162 from the blood glucose measurement unit 110.

The medical device 100 may additionally comprise a further interface 170, for example a wired interface such as a serial port, a Universal Serial Bus (USB) interface, a mini-USB interface, or a wireless interface such as an infrared (e.g. an IRDA) interface, a Bluetooth™ interface, and/or the like, in order to receive data and/or to transmit data. The interface 170 may be connected to the blood glucose measurement unit 110 in order to receive data from the blood glucose measurement unit 110 and/or to forward data to blood glucose measurement unit 110.

Additionally, the medical device 100 comprises a clock unit 180 which provides a date and time information, for example based on a clock generator, which may be displayed at the display 162. For example, the clock unit 180 may provide date and time information to the blood glucose measurement unit 110 for data processing and/or for generating a time stamp for an associated blood glucose measurement.

In the embodiment depicted in FIGS. 1 and 2 the medical device 100 further comprises an NFC antenna 193, an energy supply unit 195 and a charge control unit 196 which are all electrically connected with the measurement unit 110 and with each other. Further, these components are connected with an energy storage unit 190 formed, for example, by a rechargeable battery or a capacitor (super-cap) which provides electrical energy (voltage or current) for the components of the medical device 100. The energy storage unit 190 is therefore connected with all components of the medical device 100 for energy supply.

As outlined above, the medical device 100 comprises a blood glucose measurement unit 110. The blood glucose measurement unit 110 may be arranged to measure the blood glucose level in the blood of e.g. the user by testing a drop of blood on a test strip that is inserted into the slot 112. The measurement may be made using e.g. an electrochemical method or an optical method by the measurement unit 110. Full insertion of the test strip in the slot 112 may be detected by a respective sensor, e.g. a proximity switch, and may activate the measurement unit 110. Alternatively, the blood glucose measurement unit 110 is arranged to measure the blood glucose level of the user via infrared diagnosis or an alternative contactless measurement method.

The measurement of the blood glucose measurement may be triggered by user input which is received via user input unit 150 or based on a signal from the slot 112 detecting a test strip. Alternatively, the trigger signal may be generated automatically by the clock unit 180 or by the processor of the blood glucose measurement unit 110.

The blood glucose measurement unit 110 may comprise input ports and output ports of a microprocessor or a bus system managing the data handling between several functional units. This includes bus systems, such as e.g. Advanced Microprocessor Bus Architecture bus systems implemented in a microprocessor or external bus systems connected to a microprocessor. The blood glucose measurement unit 110 may retrieve data from the data storage 130 on demand and forwarded them to its processor, to the display unit 160 or to the interface 170. Moreover, the blood glucose measurement unit 110 may forward control signals, such as trigger signals or control signals, e.g. to the display unit 160 or the interface 170.

The data storage 130 is arranged to store data entered via the user input unit 150, a plurality of blood glucose measurement data received from the blood glucose measurement unit 110 together with a time stamp and/or at least one event tag associated to each measurement data, data calculated from the plurality of blood glucose measurement values processed by the processor 140 and/or data received via interface 170.

Furthermore, data storage 130 is arranged to provide the stored data to the processor of the blood glucose measurement unit 110, to the display unit 160 and/or to the interface 170. The data storage 130 may be implemented as a semiconductor memory such as a Flash memory. Alternatively, it is implemented as a hard disk memory or an on-chip memory of the processor of the blood glucose measurement unit 110.

The user input unit 150 may be implemented as a keyboard comprising one or more push buttons 151, 152, 153, 154. The keyboard may comprise one or more soft keys, wherein the function of the soft keys may be displayed on the display 162. Alternatively, the user input unit 150 is a key board or a touch screen. Alternatively, the user input unit 150 comprises a microphone for receiving speech input so that data can be entered via speech input.

The display unit 160 may comprise an LCD or LED display 162. In one embodiment the display may display a number of alphanumerical characters so that e.g. the presently measured blood glucose value can be displayed together with additional instructions for the user. Alternatively or additionally, the display unit 160 comprises a graphic display in order to display graphs or graphics such as icons. Further the display of the display unit 160 may comprise a touchscreen.

The interface 170 may be realized as a wireless interface, such as IRDA, Bluetooth™, GSM, UMTS, ZigBee, or WI-FI, etc. Alternatively, the interface is a wired interface, such as a USB port, mini-USB port, serial data port, parallel data port, etc., for receiving and transmitting data. In a further alternative embodiment the medical device 100 does not comprise an interface 170.

According to another alternative embodiment, medical device 100 may comprise a memory card reader or a memory card reader interface. The memory card reader may be adapted to read information from a memory card, such as a Flash memory card, or any type of SIM card. For this purpose, the memory card comprises a memory, wherein at least one of a selected algorithms together with corresponding parameters, a history of the blood glucose values and/or insulin doses administered, etc. is stored. Thus, in the case that the medical device 100 has a defect, the relevant data may still be stored on the memory card which can be easily removed from the memory card reader of the medical device 100 and transferred to a new medical device 100. Moreover, the memory card may be used in order to provide information on the history of the treatment to e.g. an HCP.

In the case that the memory card is a SIM card providing subscriber identification for a mobile communication network and the interface unit 170 is additionally a mobile communication interface, additional functions of the medical device 100 may be unlocked by the provider of the SIM card via a telecommunication channel. This offers the possibility that the medical device 100 can communicate with other telecommunication devices via predefined channels, such as UMTS or GSM. Via the international mobile subscriber identity, also called IMSI, stored in the SIM card, the medical device 100 identifies itself within the network and, thus, can be addressed via the network. In such a case the medical device 100 can be easily checked, remote controlled, updated, monitored, etc., via interface unit 170, e.g. by addressing the mobile communication unit with a phone number.

Furthermore, the medical device 100 may be able to transmit data via SMS, e-mail or via mobile internet connection. Moreover, this offers the possibility to locate the medical device 100 in an emergency case.

In the case that the blood glucose measurement unit 110 is a continuous sensor which is e.g. implanted a dose delivery unit with an insulin pump forming an automatic delivery system may be additionally provided.

Using the above medical device comprising the NFC antenna 193, the energy supply unit 190 and the charge control unit 196 it can be avoided to conduct a blood glucose measurement with too little voltage and/or charge thereby reducing the risk to measure false measurement values because the charge control unit 196 is adapted to determine the electric charge contained in the energy storage unit 190 before the blood glucose measurement is conducted by the measurement unit 110. In one embodiment, for example, the charge control unit 196 checks the charge contained in the energy storage unit 190 just after activation of the measurement unit 110 by full insertion of the strip into the slot 112. The measurement is only conducted if the electric charge contained in the energy storage unit 190 determined by the charge control unit 196 is greater than a pre-defined minimum charge value. Otherwise, a pre-defined visible, audible and/or tactile signal is produced by the display unit 160, for example a respective warning text at the display 162.

In another embodiment the charge control unit 196 activates the energy supply unit 195 for energy withdrawal using the NFC antenna 193 if the electric charge contained in the energy storage unit 190 determined by the charge control unit 196 is equal to or below a pre-defined minimum charge value.

In one embodiment the NFC antenna (also referred to as internal antenna) 193 may have a dimension of 3×3×0.5 cm, and may provide a maximum of 3 mA at 3 V.

For energy supply an external NFC antenna of a mobile phone or smart phone or another charging device may be used.

The NFC antenna 193 operates at 13.56 MHz on ISO/IEC 18000-3 air interface and at rates ranging from 106 kbit/s to 424 kbit/s. The NFC antenna 193 receives energy from an electromagnetical field produced by the external antenna 200 (see FIGS. 3 and 5).

Figures 3, 4:
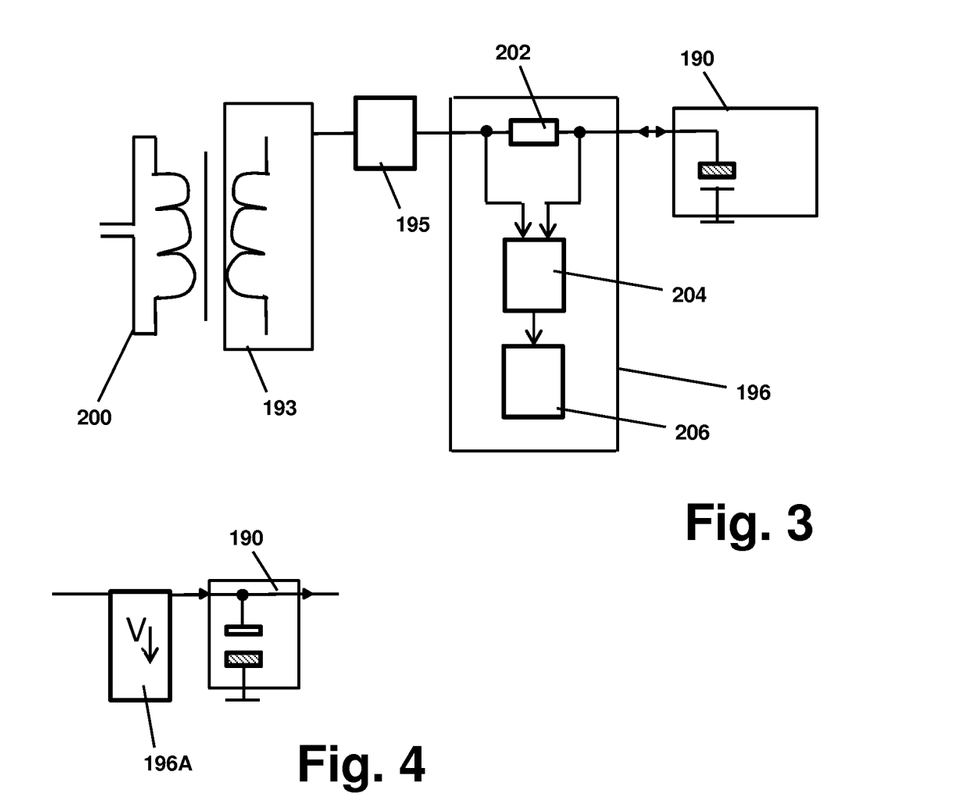
FIG. 3 depicts the circuitry of a first embodiment of a charge control unit for the medical device of FIG. 1.
FIG. 4 shows a second embodiment of a charge control unit for the medical device of FIG. 1.

In an embodiment shown in FIG. 3 the charge control unit 196 comprises a gas gauge. The gas gauge (also referred to as fuel gauge or Coulomb counter) may be used in the electronic field for the load count in an energy supply unit such as a rechargeable battery, similar to the tank meter in the car. It comprises a resistor 202 having very low resistance and a voltage meter 204 determining the voltage drop over the resistor 202 in order to determine the electric charge contained in the energy storage unit 190. The gas gauge may further comprise an A/D converter. A processor 206 of the charge control unit is connected to the clock unit 180. The A/D converter converts the measured voltage drop over the resistor 202 measured by the voltage meter 204 into an A/D converter count. The voltage drop or its A/D convertor count is added together by the processor 206 over a pre-defined time period provided by the clock unit 180 thereby determining a voltage value which reflects the level of current and its direction flowing to the energy storage unit 190. High current causes an accelerated increase of the counter value and indicates a high electric charge and low current a low increase indicating a low electric charge contained in the energy storage unit 190. Negative current causes a decrease in the counter value and indicates the discharge mode of the energy storage unit 190.

If the current is continuously observed, the charge value contained in the energy storage unit 190 can be determined.

In another embodiment shown in FIG. 4 the charge control unit 196A continuously observes time-dependent change in the voltage drop V over the energy supply unit 190, which is, for example, a capacitor. In this case each charging and decharging step causes a change in the voltage drop over the capacitor. The charge control unit observes the development of the voltage drop over time thereby determining the amount of charge flowing to or from the capacitor based on the continuous observation of the voltage drop and the well-known relation Q=C×U, wherein U is the voltage, C is the capacity of the capacitor and Q is the charge.

Figure 5:
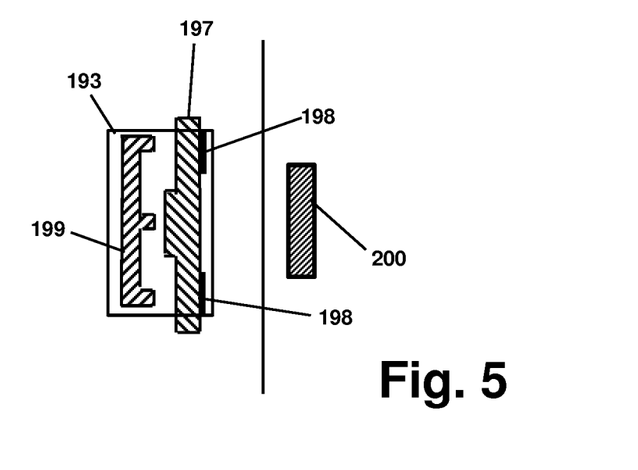
FIG. 5 shows an embodiment of a NFC antenna on a PCB.

An embodiment of an NFC antenna 193 is shown in FIG. 5. This figure depicts the PCB 197 comprising an electrical circuit on its front face. On its back face a coil 198 is attached forming the antenna. Further, the NFC antenna 193 comprises a ferrit core or disc 199 on the front side of the PCB in order provide a more efficient charging. Ferrites are electrically bad or non-conductive ferromagnetic ceramic materials from the iron oxide hematite (Fe2O3), rarely of magnetite (Fe3O4) and other metal oxides. Depending on the composition ferrites are magnetically hard or magnetically soft.

Figure 6:
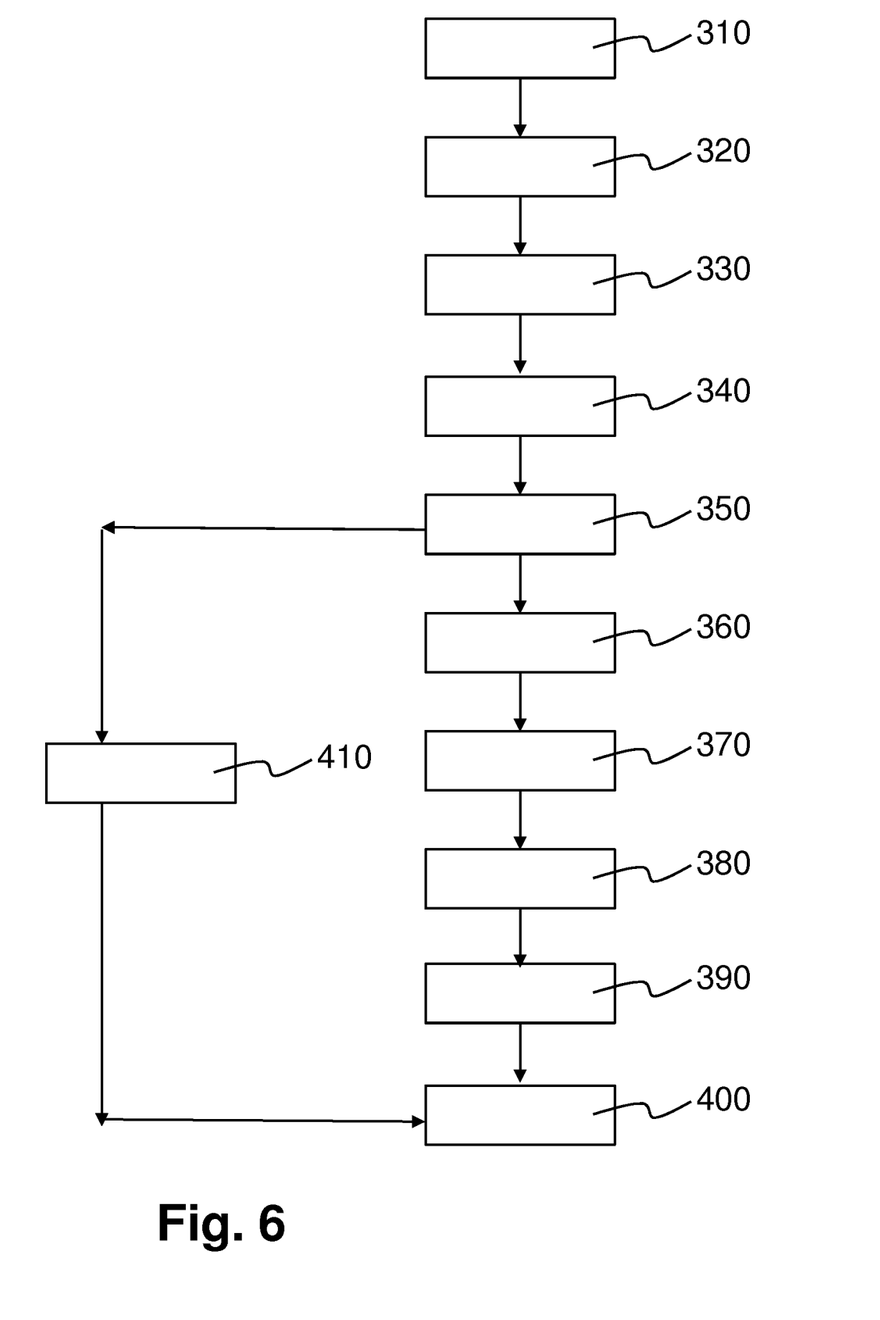
FIG. 6 depicts a flow diagram containing a procedure realized by the medical device of FIG. 1 in the "Measure BC" mode.

As shown in FIG. 6, the medical device 100 is capable to perform a number of operating processes. According to an alternative after switching on, e.g. by pressing a key 151, 152, 153 or 154, for example the confirmation key 152 for a predetermined time, or detection of a test strip within the slot 112, the medical device 100 performs initialization step 310 for initializing the functional components of the medical device 100. After this, the different operation modes which are implemented in the medical device 100, are displayed in the display step 320, for example operation modes such as "Measure BC", "Logbook" and/or "Settings".

In step 330 the user selects one of the displayed operation modes via the user input unit 150, for example by means of the keys 153, 154 for scrolling down or up, and confirms the selection using the confirmation key 152.

In step 340 the selected operation mode is executed. As an example the mode "Measure BC" is selected for executing a blood glucose measurement. Upon execution of this mode the user/patient is requested to provide a test strip with a blood sample.

In the "Logbook" mode the history of previous measurements and statistical results may be calculated and displayed. The "Settings" mode allows the user to define and change some parameters of the medical device 100.

After selecting the mode "Measure BC", in step 350 a drop of blood is applied to the test portion of the test strip which is inserted in slot 112 of the medical device 100.

According to an alternative version of the operation process steps 310 to 340 may be skipped in the case that a specific operation mode is preselected. In this case, after initialization, the preselected operation mode, which is either preselected by the user or automatically selected in accordance with a specific event, for example the detection of a fully inserted test strip in slot 112, the operating process proceeds with the following step 350 and checks the status of the energy storage unit 190 using the charge control unit 196 as indicated above. If the electric charge contained in the energy storage unit 190 determined by the charge control unit 196 is greater than the pre-defined minimum charge value, the method continues with step 360 and asks the user to apply a drop of blood to the test strip. It then executes the preselected one or more operation modes, for example the mode "Measure BC". Now in step 360 the measurement unit 110 determines e. g. by an electrochemical method the blood glucose level and displays the respective new measurement value at the display 162 using the test strip inserted into the slot 112.

In the next step 370 the clock unit 180 generates the time stamp of the present measurement comprising a date and time information. The time stamp is also displayed in display 162 and both, the present blood glucose measurement value and the associated time stamp is transferred by receiving unit 120 to the data storage 130.

In the next step 380 the processor 140 compares the time stamp of the present blood glucose measurement value with each of time ranges for tagging preselection of the events stored in the data storage 130 which events may be selected as the associated event tag. If the time stamp of the present measurement value (new measurement value), in particular the time information of the time stamp, lies within the current time range of e. g. the fasting event automatically the fasting tag is provided for confirmation by the user and displayed with a respective sign, for example a struck out, empty apple, at display 162. In order to show that a confirmation is necessary the tag sign 168 displayed on display 162 is blinking/flashing. Now, the user may confirm the fasting tag for example by pressing the confirmation key 152.

Alternatively, the user may change the tag using the up and down keys 153, 154 into the pre-meal tag, the post-meal tag or the no-tag (nil). If the correct tag is chosen the user confirms the tag by pressing the confirmation key 152. By confirmation of the tag with the confirmation key 152 the flashing of the displayed tag sign is stopped and the tag sign is displayed continuously without blinking. In this state, pressing the up/down keys 153, 154 will not change the tag. Then, the processor 140 initiates storage of the associated, confirmed tag with regard to the recent measurement value in the data storage 130 via blood glucose measurement unit 110.

If in step 380 the processor 140 cannot find any range for tagging pre-selection which refers to the time information of the time stamp of the present measurement value, the no-tag is preselected.

After pressing the confirmation key 152, if the user presses the confirmation key again, the tag will start flashing again and pressing the up/down key will again allow the user to change the tag as explained above.

Further, in the "Logbook" mode the user is allowed to change the tag in the above explained manner but only within a predefined time range from the associated time stamp of the blood glucose measurement value, for example within 10 days.

In the next optional step 390 a comment to the present measurement value may be selected by the user using the up and down keys 153, 154. The comment may then be confirmed with the confirmation key 152, wherein the chosen comment is then stored in the data storage 130 associated to the present measurement value as well.

When the medical device 100 is in the "Measure BC" mode, the device may turn into the sleep state automatically after, for example, 120 seconds without any new action. Once the device has returned a new measurement value, the device turns to the sleep state automatically after for example 60 seconds without any user interaction. The transformation into the sleep state is depicted in FIG. 6 by the step 400.

If the electric charge contained in the energy storage unit 190 determined by the charge control unit 196, 196A is equal to or below a pre-defined minimum charge value, for example 30 mAs, the method continues with step 410. In this step the display unit 160 produces a pre-defined visible, audible and/or tactile signal for the user in order to tell the user that the charge of the energy storage unit is too low and a measurement cannot be conducted at this time. For example, a respective warning message is displayed at the display 162. The method then further proceeds with step 400.

In the sleep state the charge control unit 196 may activate the energy supply unit 195 for energy withdrawal using the NFC antenna 193 if the electric charge contained in the energy storage unit determined by the charge control unit is equal to or below a pre-defined minimum charge value.

As explained above the medical device 100 provides at least one memory review mode which is called "Logbook" mode. The "Logbook" mode may be entered when the user activates the medical device 100 by pressing e.g. the confirmation button 152. In the "Logbook" the measurement values are, for example, displayed in the order in which the entries are entered into the device, or alternatively according to the time and date assigned to the measurement values. In particular the most recent blood glucose measurement value is shown upon entry into the "Logbook" mode. Pressing the up and down keys 153, 154 the user may scroll through the records, for example by pressing the down key 153 the user may scroll backwards in time and by pressing the up key 154 the user scrolls forward in time.

REFERENCE NUMBERS 100 medical device
110 blood glucose measurement unit
112 slot
130 data storage
150 user input unit
151, 153 key
154 key
152 confirmation key
160 display unit
162 display
170 interface
180 clock unit
190 energy storage unit
193 NFC antenna (internal)
195 energy supply unit
196,196A charge control unit
197 PCB with electronic circuit 198 coil
199 ferrit core
200 external NFC antenna
202 resistor
204 voltage meter
206 processor
310, 320 steps of the operation method of the medical device
330, 340 steps of the operation method of the medical device
350, 360 steps of the operation method of the medical device
370, 380 steps of the operation method of the medical device
390, 400 steps of the operation method of the medical device
410 step of the operation method of the medical device

The invention claimed is:

1. A medical device comprising:
a measurement unit adapted to perform a measurement of a value or values of a physiological parameter;
an energy storage unit connected with the measurement unit providing energy supply for the measurement unit;
an NFC antenna comprising a ferrite core or disc;
an energy supply unit connected to the NFC antenna and to the energy storage unit, wherein the energy supply unit controls the NFC antenna such that in the presence of an electromagnetic field of a pre-defined frequency range, energy is withdrawn from the electromagnetic field surrounding the NFC antenna and stored in the energy storage unit;
a charge control unit, connected to the energy storage unit and adapted to determine a charge value representing an electric charge contained in the energy storage unit, wherein the charge control unit is adapted to determine the charge value before a measurement of the physiological parameter is performed by the measurement unit; and
a communication unit connected with the charge control unit, wherein the communication unit is adapted to output a pre-defined visible, audible, and/or tactile signal if the charge value determined by the charge control unit is equal to or below a pre-defined minimum charge value,
wherein the measurement unit is adapted such that a measurement of a value or values of the physiological parameter performed by the measurement unit is blocked if the charge value determined by the charge control unit is equal to or below the pre-defined minimum charge value.

2. The medical device according to claim 1, wherein the charge control unit comprises a gas gauge.

3. The medical device according to claim 1, wherein the NFC antenna is formed by a structure printed on a PCB.

4. The medical device according to claim 1, wherein the charge control unit is connected to the energy supply unit, wherein the charge control unit activates the energy supply unit for energy withdrawal using the NFC if the charge value determined by the charge control unit is equal to or below the pre-defined minimum charge value.

5. The medical device according to claim 4, wherein in a sleep state, the charge control unit activates the energy supply unit for energy withdrawal using the NFC antenna responsive to determining, by the charge control unit, that the charge value is equal to or below the pre-defined minimum charge value.

6. The medical device according to claim 4, wherein the pre-defined minimum charge value is 30 mAs.

7. The medical device according to claim 1, wherein the medical device is adapted to administrate a medicament based on the value or values of the physiological parameter.

8. The medical device according to claim 1, wherein the physiological parameter is a blood glucose level.

9. The medical device according to claim 1, wherein the energy storage unit is a rechargeable battery.

10. The medical device according to claim 1, further comprising an integrated temperature tracker configured to determine a temperature and prevent measurement of the physiological parameter by the measurement unit based on the determined temperature.

11. A method for operating a medical device comprising a measurement unit adapted to perform a measurement of a value or values of a physiological parameter and an NFC antenna configured to withdraw energy from an electromagnetic field surrounding the NFC antenna to store in an energy storage unit of the medical device, the NFC antenna comprising a ferrite core or disc, wherein the method comprises:
determining, by a charge control unit of the medical device, a charge value representing an electric charge contained in the energy storage unit of the medical device before one measurement of a physiological parameter is conducted by a measurement unit of the medical device; and
blocking a measurement of a value or values of the physiological parameter performed by the measurement unit and outputting a pre-defined visible, audible, and/or tactile signal by a communication unit of the medical device if the charge value determined by the charge control unit is equal to or below a pre-defined minimum charge value such that the measurement of the value or values of the physiological parameter is performed by the measurement unit of the medical device only if the charge value determined by the charge control unit of the medical device is greater than the pre-defined minimum charge value.

12. The method according to claim 11, further comprising operating the NFC antenna such that, in the presence of an electromagnetic field of a pre-defined frequency range, the energy is withdrawn-from the electromagnetic field surrounding the NFC antenna and stored in the energy storage unit.

13. The method according to claim 11, further comprising activating an energy supply unit of the medical device for energy withdrawal using the NFC antenna of the medical device if the charge value determined by the charge control unit is equal to or below the pre-defined minimum charge value.

14. The method according to claim 13, wherein the NFC antenna is formed by a structure printed on a PCB.

15. The method according to claim 11, wherein the physiological parameter is a blood glucose level.

16. The method according to claim 11, wherein the energy storage unit is a rechargeable battery.

17. The method according to claim 11, further comprising administering a medicament based on the value or values of the physiological parameter.

18. The method according to claim 11, wherein the charge control unit comprises a gas gauge.

19. The method according to claim 11, further comprising preventing a measurement of a value or values of the physiological parameter if a temperature value detected by a temperature tracker of the medical device is below or equal to a minimum temperature value or above or equal to a maximum temperature value.

20. The method according to claim 11, wherein the pre-defined minimum charge value is 30 mAs.

* * * * *